US012797528B2

(12) United States Patent
McGuire et al.

(10) Patent No.: US 12,797,528 B2
(45) Date of Patent: Nov. 17, 2026

(54) BIODEGRADABLE ELECTROCHEMICAL DEVICE WITH BARRIER LAYER

(71) Applicants: XEROX CORPORATION, Norwalk, CT (US); NATIONAL RESEARCH COUNCIL OF CANADA, Ottawa (CA)

(72) Inventors: Gregory McGuire, Oakville (CA); Naveen Chopra, Oakville (CA); Nan-Xing Hu, Oakville (CA); Alexis Laforgue, Montreal (CA); Nathalie Chapleau, Montreal (CA)

(73) Assignees: XEROX CORPORATION, Norwalk, CT (US); NATIONAL RESEARCH COUNCIL OF CANADA, Ottawa (CA)

( * ) Notice: Subject to any disclaimer, the term of this patent is extended or adjusted under 35 U.S.C. 154(b) by 539 days.

(21) Appl. No.: 18/284,244

(22) PCT Filed: Mar. 30, 2022

(86) PCT No.: PCT/US2022/022475
§ 371 (c)(1),
(2) Date: Sep. 26, 2023

(87) PCT Pub. No.: WO2022/212454
PCT Pub. Date: Oct. 6, 2022

(65) Prior Publication Data

US 2024/0178490 A1 May 30, 2024

Related U.S. Application Data

(60) Provisional application No. 63/168,680, filed on Mar. 31, 2021.

(51) Int. Cl.
*H01M 50/122* (2021.01)
*A61M 1/14* (2006.01)
(Continued)

(52) U.S. Cl.
CPC ............. *A61M 1/287* (2013.01); *A61M 1/15* (2022.05); *A61M 1/1562* (2022.05);
(Continued)

(58) Field of Classification Search
None
See application file for complete search history.

(56) References Cited

U.S. PATENT DOCUMENTS

2011/0076511 A1 3/2011 Paolilli et al.
2012/0141766 A1 6/2012 Paulino et al.

FOREIGN PATENT DOCUMENTS

CN 110391359 A 10/2019
JP 2001155694 A 6/2001
(Continued)

OTHER PUBLICATIONS

Machine translation of JP2001155694 (Year: 2001).*
(Continued)

*Primary Examiner* — Wyatt P Mcconnell
(74) *Attorney, Agent, or Firm* — MH2 Technology Law Group LLP

(57) ABSTRACT

An electrochemical device is disclosed and may include an electrolyte composition disposed between the anode and the cathode and a water vapor barrier which may include a biodegradable material, where the water vapor barrier is disposed to prevent water vapor escaping from the electrochemical device. The water vapor barrier further may include poly lactic acid or a metalized coating. The water vapor barrier further may further include multiple layers and have a water vapor transmission rate (WVTR) less than or equal to 2 wt % over 24 hours. Embodiments of the water vapor barrier may also include a polymeric biodegradable material or a metalized coating disposed onto the biodegradable material. The water vapor barrier may also include
(Continued)

multiple layers and may have a water vapor transmission rate (WVTR) less than or equal to 1 mg per $cm^2$ over 24 hours.

19 Claims, 7 Drawing Sheets

(51) Int. Cl.

| | |
|---|---|
| ***A61M 1/16*** | (2006.01) |
| ***A61M 1/28*** | (2006.01) |
| ***A61M 39/28*** | (2006.01) |
| ***H01M 50/119*** | (2021.01) |
| ***H01M 50/121*** | (2021.01) |
| ***H01M 50/131*** | (2021.01) |

(52) U.S. Cl.

CPC ........ *A61M 1/1656* (2013.01); *A61M 1/1672* (2014.02); *A61M 39/281* (2013.01); *H01M 50/119* (2021.01); *H01M 50/121* (2021.01); *H01M 50/122* (2021.01); *H01M 50/131* (2021.01); *A61M 2205/15* (2013.01); *A61M 2205/3317* (2013.01); *A61M 2205/3331* (2013.01); *A61M 2205/3368* (2013.01)

(56) References Cited

FOREIGN PATENT DOCUMENTS

| | | | |
|---|---|---|---|
| JP | 2014049307 | A | 3/2014 |
| WO | 2020046932 | A1 | 3/2020 |
| WO | 2021/034899 | A8 | 2/2021 |
| WO | 2021034899 | A1 | 2/2021 |

OTHER PUBLICATIONS

Arias-Kraska, Agnieszka (ISA Authorized Officer), "PCT Notification of Transmittal of the International Search Report and the Written Opinion of the International Searching Authority, or the Declaration," mailed Jul. 19, 2022 in corresponding PCT Application No. PCT/US2022/022475, 11 pages.

CN Office Action for CN Application No. 202280026314.1, dated Dec. 12, 2025.

Requisition by the Examiner issued Sep. 4, 2024 in corresponding Canadian Application No. 3,213,871, 4 pages.

Japanese Office Action fo JP Application No. 2023-558628, dated Mar. 6, 2026.

* cited by examiner

BIODEGRADABLE ELECTROCHEMICAL DEVICE WITH BARRIER LAYER

CROSS-REFERENCE TO RELATED APPLICATIONS

This patent application is a national stage entry from International Application No. PCT/US2022/022475, filed on Apr. 21, 2021, published as International Publication No. WO 2022/212454 A1 on Mar. 30, 2022, and claims the benefit of U.S. Provisional Patent Application No. 63/168,380, filed on Mar. 31, 2021, the entire contents of all of which are incorporated by reference herein.

TECHNICAL FIELD

The presently disclosed embodiments or implementations are directed to biodegradable electrochemical devices, solid aqueous electrolytes thereof, and moisture barriers for the same.

BACKGROUND

The number of batteries being produced in the world is continuously increasing as a consequence of the growing need for portable and remote power sources. Particularly, a number of new technologies require batteries to power embedded electronics. For example, embedded electronics, such as portable and wearable electronics, Internet of Things (IOT) devices, patient healthcare monitoring, structural monitoring, environmental monitoring, smart packaging, or the like, rely on batteries for power. While conventional batteries may be partially recycled, there are currently no commercially available batteries that are environmentally friendly or biodegradable. As such, an increase in the manufacture and use of conventional batteries results in a corresponding increase in toxic and harmful waste in the environment if not properly disposed of or recycled. In view of the foregoing, there is a need to develop biodegradable batteries; especially for applications that utilize disposable batteries for a limited time before being discarded.

Further, to meet the demand for flexible, low-cost, medium or low performance batteries, all-printed batteries have been developed, that are commercially available as single-use disposable batteries. However, none of these all-printed batteries are biodegradable.

It is generally accepted that one of the greatest challenges to producing biodegradable batteries is the development of a biodegradable polymer electrolyte, which is the main polymer-based component of an all-printed battery. Moreover, the development of such a biodegradable polymer electrolyte that can also be printed using existing printing technologies is an additional challenge.

Conventional biodegradable polymer electrolytes may often include a combination of a biodegradable polymer and a conductive salt. To obtain the biodegradable polymer electrolyte, the biodegradable polymer and the conductive salt are dissolved in a solvent, and then the solvent is subsequently evaporated at a relatively slow rate to produce a solid polymer electrolyte film. These conventional biodegradable polymer electrolytes often suffer from low ionic conductivity (e.g., less than about $10^{-5}$ S/cm at RT) at ambient temperature due to the low mobility of the ions in the biodegradable polymer. Sufficient conductivity, however, may be achieved when the polymer electrolyte is heated to a temperature sufficient (i.e., an operational temperature) to allow polymer chain mobility, thereby allowing the ions to move more freely through the polymer electrolyte structure. Sufficient conductivity may also be achieved by incorporating additives that suppress the crystallinity of the polymer electrolyte, thereby decreasing the operational temperature thereof. As such, biodegradable polymer electrolytes that may be operated with sufficient conductivity at room temperature is limited.

In addition to the foregoing drawbacks, conventional biodegradable polymer electrolytes also suffer from lengthy manufacturing processes due to the time required to evaporate the solvent during manufacture. For example, several hours of evaporation aided by vacuum and/or temperature are often required to evaporate the solvent to prepare the conventional biodegradable polymer electrolytes, thereby limiting the compatibility of conventional biodegradable polymer electrolytes with high-throughput printing processes where successive layers must be printed on top of each other in a matter of minutes.

While printable, biodegradable electrochemical devices, solid aqueous electrolytes thereof, and methods for synthesizing and fabricating the same are available, the layers of various materials, including current collectors, cathode/anode materials, binders, adhesives, and electrolyte need to be printed with high fidelity and accuracy. Furthermore, the retention of moisture or water content within the aqueous electrolyte is critical to battery performance via maintenance of solubilized salts for good ion conductivity and printed biodegradable batteries such as these suffer from shortened lifespan due to water losses via evaporation through the biodegradable substrate, such as polylactic acid (PLA) film. There is a need to improve the moisture retention rates of these batteries, and in particular, the electrolyte layer, by reducing the WVTR (water vapor transmission rate). At the same time, a challenge remains to achieve this sealing property to surround the electrochemical device whilst maintaining or reducing the non-biodegradable content of printed biodegradable batteries, which is currently not possible with the use of conventional relatively thick, non-biodegradable foil 'pouches' to seal printed batteries such as those found in Li-ion batteries.

SUMMARY

The following presents a simplified summary in order to provide a basic understanding of some aspects of one or more embodiments of the present teachings. This summary is not an extensive overview; nor is it intended to identify key or critical elements of the present teachings, nor to delineate the scope of the disclosure. Rather, its primary purpose is merely to present one or more concepts in simplified form as a prelude to the detailed description presented later.

An electrochemical device is disclosed. The electrochemical device also includes an anode and a cathode. The device also includes an electrolyte composition disposed between the anode and the cathode and a water vapor barrier which may include a biodegradable material, where the water vapor barrier is disposed to prevent water vapor escaping from the electrochemical device. The water vapor barrier further may include polylactic acid. The water vapor barrier further may include a metalized or aluminum metalized coating. The water vapor barrier further may further include multiple layers. The electrochemical device further may have a water vapor transmission rate (WVTR) less than or equal to 2 wt % over 24 hours.

Embodiments of the water vapor barrier may also include a biodegradable material, which may include a polymer. The water vapor barrier may also include a metalized coating disposed onto the biodegradable material. The water vapor barrier may include a polymer which may further include polylactic acid, a metalized or aluminum metalized coating. The water vapor barrier may also include multiple layers and may have a water vapor transmission rate (WVTR) less than or equal to 1 mg per $cm^2$ over 24 hours.

BRIEF DESCRIPTION OF THE DRAWINGS

The accompanying drawings, which are incorporated in and constitute a part of this specification, illustrate embodiments of the present teachings. These and/or other aspects and advantages in the embodiments of the disclosure will become apparent and more readily appreciated from the following description of the various embodiments, taken in conjunction with the accompanying drawings of which.

Figure 1:
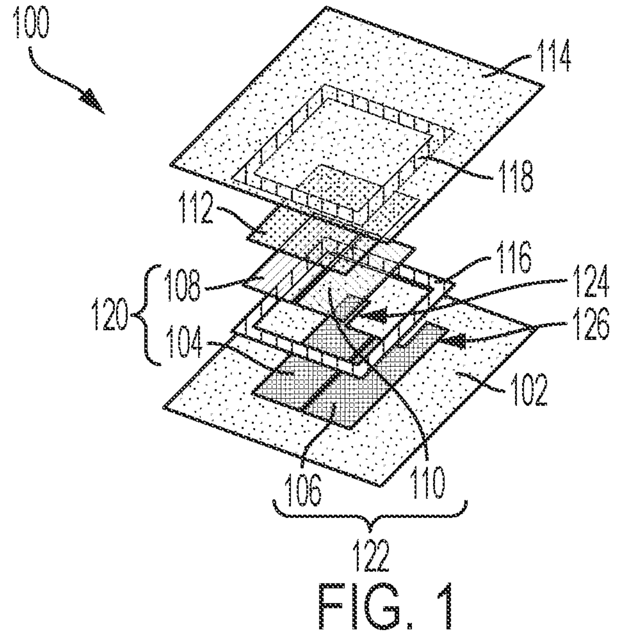
FIG. 1 illustrates an exploded view of an exemplary biodegradable electrochemical device in a side-by-side configuration, according to one or more embodiments disclosed.

It should be noted that some details of the figures have been simplified and are drawn to facilitate understanding of the present teachings rather than to maintain strict structural accuracy, detail, and scale.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes embodiments containing A, B, or C, multiple examples of A, B, or C, or combinations of A/B, A/C, B/C, A/B/B/B/B/C, A/B/C, etc. In addition, throughout the specification, the meaning of "a," "an," and "the" include plural references. The meaning of "in" includes "in" and "on."

Reference will now be made in detail to exemplary embodiments of the present teachings, examples of which are illustrated in the accompanying drawings. Wherever possible, the same reference numbers will be used throughout the drawings to refer to the same, similar, or like parts.

A biodegradable electrochemical device is disclosed herein. As used herein, the term "biodegradable" or "biodegradable material" may refer to a material, component, substance, device, or the like, capable of or configured to be decomposed by living organisms, particularly microorganisms in a landfill within a reasonable amount of time. The material, component, substance, device, or the like may be decomposed into water, naturally occurring gases like carbon dioxide and methane, biomass, or combinations thereof. As used herein, the expression "biodegradable electrochemical device" or "biodegradable device" may refer to an electrochemical device or a device, respectively, where at least one or more components thereof is biodegradable. In some instances, a majority or substantial number of the components of the biodegradable electrochemical device or the biodegradable device are biodegradable. In other instances, all of the polymer components of the biodegradable electrochemical device or the biodegradable device are biodegradable. For example, the polymers and/or other organic-based components of the electrochemical device are biodegradable while the inorganic materials of the electrochemical device disclosed herein, including the metals and/or metal oxides, may not be biodegradable. It should be appreciated that if all polymer and/or organic-based components of an electrochemical device are biodegradable, it is generally accepted that the complete electrochemical device is considered biodegradable. As used herein, the term "compostable" may refer to items that are able to be made into compost or otherwise disposed of in a sustainable or environmentally friendly manner. Compostable materials may be considered to be a subset category of biodegradable materials wherein additional specific environmental temperatures or conditions may be needed to break down a compostable material. While the term compostable is not synonymous with biodegradable, they may be used interchangeably in some instances, wherein the conditions necessary to break down or decompose a biodegradable material are understood to be similar to the conditions necessary to break down a compostable material. As used herein, the term or expression "electrochemical device" may refer to a device that converts electricity into chemical reactions and/or vice-versa. Illustrative electrochemical devices may be or include, but are not limited to, batteries, die-sensitized solar cells, electrochemical sensors, electrochromic glasses, fuel cells, electrolysers, or the like.

As used herein, the term or expression "environmentally friendly electrochemical device" or "environmentally friendly device" may refer to an electrochemical device or device, respectively, that exhibits minimal, reduced, or no toxicity to the ecosystems or the environment in general. In at least one embodiment, the electrochemical devices and/or components thereof disclosed herein are environmentally friendly.

As used herein, the term or expression "film" or "barrier layer" may refer to a thin, partially or substantially plastic and/or polymeric material that may be used in various electrochemical device components or parts, including, but not limited to substrates, connections, enclosures, barriers, or combinations thereof. Films as described herein may be rigid or flexible, depending upon the inherent physical properties or dimensions of their respective compositions. In at least one embodiment, these films or barrier layers may be environmentally friendly or biodegradable As used herein, the term or expression "enclosure," "barrier," or "water vapor barrier" may refer to materials utilized in partially sealed, fully sealed or otherwise used to prevent moisture, water or other evaporable materials from entering or exiting via the barrier of an electrochemical device. In at least one embodiment, these enclosures may be environmentally friendly or biodegradable.

As used herein, the term or expression "metal layer" may refer to a layer of metal on a surface, film, substrate, or barrier layer. A metal layer, as described herein may include examples of metalized coatings, which may be deposited onto a surface by means of a vapor or chemical deposition process, as well as metal layers including metal foils, metal films, or other metal layers combined with or adhered to a surface, film, substrate, or barrier layer.

In at least one embodiment, the biodegradable electrochemical device disclosed herein may include an anode, a cathode (i.e., a current collector and/or an active layer), and one or more electrolyte compositions (e.g., a biodegradable solid aqueous electrolyte composition). In another embodiment, the biodegradable electrochemical device may further include one or more substrates, one or more seals, one or more packages, one or more pouches, one or more enclosures, or combinations thereof.

The biodegradable electrochemical devices disclosed herein may be flexible. As used herein, the term "flexible" may refer to a material, device, or components thereof that is capable of being bent around a predetermined radius of curvature without breaking and/or cracking. The biodegradable electrochemical devices and/or the components thereof disclosed herein may be bent around a radius of curvature of about 30 cm or less, about 20 cm or less, about 10 cm or less, about 5 cm or less without breaking or cracking.

FIG. 1 illustrates an exploded view of an exemplary biodegradable electrochemical device 100 in a side-by-side or coplanar configuration, according to one or more embodiments. As illustrated in FIG. 1, the biodegradable electrochemical device 100 may include a first substrate 102, first and second current collectors 104, 106 disposed adjacent to or on top of the first substrate 102, an anode active layer 108 disposed adjacent to or on top of the first current collector 104, a cathode active layer 110 disposed adjacent to or on top of the second current collector 106, an electrolyte layer 112 disposed adjacent to or on top of the anode active layer 108 and the cathode active layer 110, and a second substrate 114 disposed adjacent to or on top of the electrolyte composition 112. It should be appreciated that the first current collector 104 and the anode active layer 108 may be collectively referred to herein as an anode 120 of the biodegradable electrochemical device 100. It should further be appreciated that the second current collector 106 and the cathode active layer 110 may be collectively referred to herein as a cathode 122 of the biodegradable electrochemical device 100. As illustrated in FIG. 1, the anode 120 and the cathode 122 of the biodegradable electrochemical device 100 may be coplanar such that the anode 120 and the cathode 122 are arranged along the same X-Y plane.

In at least one embodiment, the biodegradable electrochemical device 100 may include one or more seals (two are shown 116, 118) capable of or configured to seal or hermetically seal the current collectors 104, 106, the anode active layer 108, the cathode active layer 110, and the electrolyte composition 112 between the first and second substrates 102, 114 of the biodegradable electrochemical device 100. For example, as illustrated in FIG. 1, the biodegradable electrical device 100 may include two seals 116, 118 interposed between the first and second substrates 102, 114 and about the current collectors 104, 106, the anode active layer 108, the cathode active layer 110, and the electrolyte composition 112 to seal or hermetically seal the biodegradable electrochemical device 100. In another embodiment, the biodegradable electrochemical device 100 may be free or substantially free of seals 116, 118. For example, the substrates 102, 114 may be melted or bonded with one another to seal the biodegradable electrochemical device 100.

Figure 2:
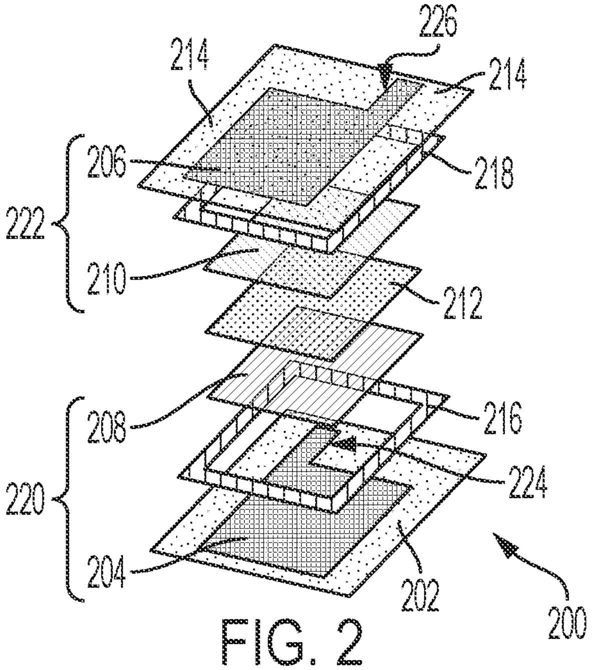
FIG. 2 illustrates an exploded view of another exemplary biodegradable electrochemical device in a stacked configuration, according to one or more embodiments disclosed.

FIG. 2 illustrates an exploded view of another exemplary biodegradable electrochemical device 200 in a stacked configuration, according to one or more embodiments. As illustrated in FIG. 2, the biodegradable electrochemical device 200 may include a first substrate 202, a first current collectors 204 disposed adjacent to or on top of the first substrate 102, an anode active layer 208 disposed adjacent to or on top of the first current collector 204, an electrolyte layer 212 disposed adjacent to or on top of the anode 108, a cathode active layer 210 disposed adjacent to or on top of the electrolyte composition 212, a second current collector 206 disposed adjacent to or on top of the cathode active layer 210, and a second substrate 214 disposed adjacent to or on top of the second current collector 206. It should be appreciated that the first current collector 204 and the anode active layer 208 may be collectively referred to herein as an anode 220 of the biodegradable electrochemical device 200. It should further be appreciated that the second current collector 206 and the cathode active layer 210 may be collectively referred to herein as a cathode 222 of the biodegradable electrochemical device 200. As illustrated in FIG. 2, the anode 220) and the cathode 222 of the biodegradable electrochemical device 200 may be arranged in a stacked configuration or geometry such that the anode 220) and the cathode 222 are disposed on top of or below one another.

In at least one embodiment, the biodegradable electrochemical device 200 may include one or more seals (two are shown 216, 218) capable of or configured to hermetically seal the current collectors 204, 206, the anode active layer 208, the cathode active layer 210, and the electrolyte composition 212 between the first and second substrates 202, 214 of the biodegradable electrochemical device 200. For example, as illustrated in FIG. 2, the biodegradable electrical device 200 may include two seals 216, 218 interposed between the first and second substrates 202, 214 and about the current collectors 204, 206, the anode active layer 208, the cathode active layer 210, and the electrolyte composition 212 to hermetically seal the biodegradable electrochemical device 200. In another embodiment, the biodegradable electrochemical device 200 may be free or substantially free of seals 216, 218. For example, the substrates 202, 214 may be melted or bonded with one another to seal the biodegradable electrochemical device 200.

As illustrated in FIGS. 1 and 2, each of the current collectors 104, 106, 204, 206 may include a respective tab 124, 126, 224, 226 that may extend outside the seals 116, 118, 216, 218 to thereby provide connectivity.

In at least one embodiment, any one or more of the substrates 102, 114, 202, 214 of the respective biodegradable electrochemical devices 100, 200 may be or include, but is not limited to, a biodegradable substrate. Illustrative biodegradable substrates may be or include, but are not limited to, one or more of polylactic acid (PLA), polylactic-co-glycolic acid (PLGA), silk-fibroin, chitosan, polycaprolactone (PCL), polyhydroxy butyrate (PHB), rice paper, cellulose, or combinations or composites thereof.

The biodegradable substrates of the respective biodegradable electrochemical devices 100, 200 may be stable at temperatures of from about 50° C. to about 150° C. As used herein, the term "stable" or "stability" may refer to the ability of the substrate to resist dimensional changes and maintain structural integrity when exposed to temperature of from about 50° C. to about 150° C. For example, the biodegradable substrates may be capable of or configured to maintain structural integrity with dimensional changes of less than about 20%, less than about 15%, or less than about 10% after exposure to temperatures of from about 50° C. to about 150° C. In one example, each of the biodegradable substrates may be stable (e.g., dimensional changes less than 20%) at a temperature of from about 50° C., about 60° C., about 70° C., about 80° C. about 90° C., about 100° C., or about 110° C. to about 120° C., about 130° C., about 140° C., or about 150° C. In another example, each of the biodegradable substrates may be stable at a temperature of at least 100° C., at least 105° C., at least 110° C., at least 115° C., at least 120° C., at least 125° C., at least 130° C., at least 135° C., at least 140° C., or at least 145° C. In at least one embodiment, the biodegradable substrates may be stable at temperatures of from about 50° C. to about 150° C. for a period of from about 5 min to about 60 min or greater. For example, the biodegradable substates may be stable at the aforementioned temperatures for a period of time of from about 5 min, about 10 min, about 20 min, or about 30 min to about 40 min, about 45 min, about 50) min, about 60) min, or greater.

In at least one embodiment, the biodegradable substrate is weldable, bondable, and/or permanently thermo-sealable without the use of an additional adhesive. For example, the biodegradable substrates of each of the substrates 102, 114, 202, 214 may be weldable and/or bondable with one another without the use of the respective seals 116, 118, 216, 218. Illustrative biodegradable substrates that may be weldable and/or bondable with one another may be or include, but are not limited to, thermoplastics, such as polylactic acid (PLA), polylactides modified with a nucleating agent to enhance crystallinity, such as polylactide modified with nucleating agent D (PLA-D) and polylactide modified with nucleating agent E (PLA-E), poly butylene succinate (PBS), poly butylene adipate terephthalate (PBAT), blends of PLA and polyhydroxy butyrate (PHB), PHB-based blends, or the like, or combinations thereof. As used herein, the term or expression "bondable," "weldable," and/or "permanently thermo-sealable" may refer to an ability of a material (e.g., substrate) to heat seal two surfaces with one another or permanently join two surfaces with one another via heating or melting.

The anode active layer 108, 208 of the respective biodegradable electrochemical devices 100, 200 may be or include, but is not limited to, one or more of zinc (Zn), lithium (Li), carbon (C), cadmium (Cd), nickel (Ni), magnesium (Mg), magnesium alloys, zinc alloys, or the like, or combinations and/or alloys thereof. Illustrative anode active layers or materials thereof may be or include, but are not limited, or the like, or combinations thereof. In at least one embodiment, the anode active layer may include zinc oxide (ZnO) in a sufficient amount to regulate or control H2 gassing.

In at least one embodiment, the anode active layer 108, 208 of the respective biodegradable electrochemical devices 100, 200 may be prepared or fabricated from an anode paste. For example, the anode active layer may be prepared from a zinc anode paste. The anode paste may be prepared in an attritor mill. In at least one embodiment, stainless steel shot may be disposed in the attritor mill to facilitate the preparation of the anode paste. The anode paste may include one or more metal or metal alloys, one or more organic solvents, one or more styrene-butadiene rubber binders, or combinations thereof. In an exemplary embodiment, the anode paste may include one or more of ethylene glycol, a styrene-butadiene rubber binder, zinc oxide (ZnO), bismuth (III) oxide ($Bi_2O_3$), Zn dust, or combinations thereof. Illustrative organic solvents are known in the art and may be or include, but are not limited to, ethylene glycol, acetone, NMP, or the like, or combinations thereof. In at least one embodiment, any one or more biodegradable binders may be utilized in lieu of or in combination with a styrene-butadiene rubber binder.

The cathode active layer 110, 210 of the respective biodegradable electrochemical devices 100, 200 may be or include, but are not limited to, one or more of iron (Fe), iron (VI) oxide, mercury oxide (HgO), manganese (IV) oxide ($MnO_2$), carbon (C), carbon-containing cathodes, gold (Au), molybdenum (Mo), tungsten (W), molybdenum trioxide ($MoO_3$), silver oxide ($Ag_2O$), copper (Cu), vanadium oxide ($V_2O_5$), nickel oxide (NiO), copper iodide ($Cu_2I_2$), copper chloride (CuCl), or the like, or combinations and/or alloys thereof. In an exemplary embodiment, the cathode active layer 110, 210 may include manganese (IV) oxide. The carbon and/or carbon-containing cathode active layers may be utilized in aqueous metal-air batteries, such as zinc air batteries.

In at least one embodiment, the cathode active layer 110, 210 may include one or more additives capable of or configured to at least partially enhance the electronic conductivity of the cathode active layer 110, 210. Illustrative additives may be or include, but are not limited to, carbon particles, such as graphite, carbon nanotubes, carbon black, or the like, or the like, or combinations thereof.

In at least one embodiment, the cathode active layer 110, 210 of the respective biodegradable electrochemical devices 100, 200 may be prepared or fabricated from a cathode paste. For example, the cathode active layer 110, 210 may be prepared from a manganese (IV) oxide cathode paste. The cathode paste may be prepared in an attritor mill. In at least one embodiment, stainless steel shot may be disposed in the attritor mill to facilitate the preparation of the cathode paste. The cathode paste may include one or more metal or metal alloys, one or more organic solvents (e.g., ethylene glycol), one or more styrene-butadiene rubber binders, or combinations thereof. In an exemplary embodiment, the cathode paste may include one or more of ethylene glycol, a styrene-butadiene rubber binder, manganese (IV) oxide ($MnO_2$), graphite, or combinations thereof. Illustrative organic solvents are known in the art and may be or include, but are not limited to, ethylene glycol, acetone, NMP, or the like, or combinations thereof. In at least one embodiment, the one or more organic solvents may be replaced or used in combination with an aqueous solvent, such as water. For example, water may be utilized in combination with manganese (IV) oxide.

The anode and/or cathode paste may have a viscosity of from about 100 cP to about 1E6 cP. For example, the anode and/or cathode paste may have a viscosity of from greater than or equal to about 100 cP, greater than or equal to about 200 cP, greater than or equal to about 500 cP, greater than or equal to about 1,000 cP, greater than or equal to about 1,500 cP, greater than or equal to about 2,000 cP, greater than or equal to about 10,000 cP, greater than or equal to about 20,000 cP, greater than or equal to about 50,000 cP, greater than or equal to about 1E5 cP, greater than or equal to about 1.5E5 cP, greater than or equal to about 2E5 cP, greater than or equal to about 3E5 cP, greater than or equal to about 4E5 cP, greater than or equal to about 5E5 cP, greater than or equal to about 6E5 cP, greater than or equal to about 7E5 cP, greater than or equal to about 8E5 cP, or greater than or equal to about 9E5 cP. In another example, the anode and/or cathode paste may have a viscosity of less than or equal to about 200 cP, less than or equal to about 500 cP, less than or equal to about 1,000 cP, less than or equal to about 1,500 cP, less than or equal to about 2,000 cP, less than or equal to about 10,000 cP, less than or equal to about 20,000 cP, less than or equal to about 50,000 cP, less than or equal to about 1E5 cP, less than or equal to about 1.5E5 cP, less than or equal to about 2E5 cP, less than or equal to about 3E5 cP, less than or equal to about 4E5 cP, less than or equal to about 5E5 cP, less than or equal to about 6E5 cP, less than or equal to about 7E5 cP, less than or equal to about 8E5 cP, less than or equal to about 9E5 cP, or less than or equal to about 1E6 cP.

In at least one embodiment, each of the anodes 120, 220) and the cathodes 122, 222, or the active layers 108, 110, 208, 210 thereof may independently include a biodegradable binder. The function of the biodegradable binder is to anchor the particles of each of the respective layers together and provide adhesion to the substrate underneath, the respective layers being the anode current collector 104, 204, the cathode current collector 106, 206, the anode active layer 108, 208, the cathode active layer 110, 210, or combinations thereof. Illustrative biodegradable binders may be or include, but are not limited to, one or more of chitosan, polylactic-co-glycolic acid (PLGA), gelatin, xanthan gum, cellulose acetate butyrate (CAB), polyhydroxy butyrate (PHB), or a combinations thereof. In at least one embodiment, any one or more of the biodegradable polymers disclosed herein with regard to the electrolyte composition may also be utilized as the biodegradable binder of the anode 120, 220, the cathode 122, 222, components thereof, or any combination thereof. As further described herein, the one or more biodegradable polymers may be cross-linked. As such, the biodegradable binders utilized for the anode 120, 220, the cathode 122, 222, and/or the components thereof, may include the cross-linked biodegradable binders disclosed herein with regard to the electrolyte composition.

The electrolyte layer 112, 212 of each of the respective biodegradable electrochemical devices 100, 200 may be or include an electrolyte composition. The electrolyte composition may utilize biodegradable polymeric materials. The electrolyte composition may be a solid, aqueous electrolyte composition. The solid, aqueous electrolyte composition may be or include a hydrogel of a copolymer and a salt dispersed in and/or throughout the hydrogel. The copolymer may include at least two polycaprolactone (PCL) chains attached with a polymeric center block (CB). For example, the copolymer may be a block copolymer or a graft copolymer including at least two PCL chains coupled with the polymeric center block, such as PCL-CB-PCL. In another example, the copolymer may be a block copolymer or a graft copolymer including at least one or more of polylactic acid (PLA), polyglycolic acid (PGA), polyethylene imine (PEI) or combinations thereof, coupled with the polymeric center block.

The copolymer or the solids may be present in the hydrogel in an amount of from about 5 weight % or greater to 90 weight % or less, based on a total weight of the hydrogel (e.g., total weight of solvent, polymer, and salt). For example, the copolymer may be present in an amount of from about 5 weight % or greater, 10 weight % or greater, 15 weight % or greater, 20 weight % or greater, 25 weight % or greater, 30 weight % or greater, 35 weight % or greater, based on a total weight of the hydrogel. In another example, the copolymer may be present in an amount of from 90 weight % or less, 80 weight % or less, 70 weight % or less, or 60 weight % or less, based on a total weight of the hydrogel. In a preferred embodiment, the copolymer or the solids may be present in the hydrogel in an amount of from about 5 weight % to about 60 weight %, about 5 weight % to about 50 weight %, about 20 weight % to about 40 weight %, or about 30 weight %, based on a total weight of the hydrogel. In yet another preferred embodiment, the copolymer or the solids may be present in the hydrogel in an amount of from greater than 30 weight % to 60 weight %, based on a total weight of the hydrogel.

The copolymer may be present in the hydrogel in an amount sufficient to provide a continuous film or layer that is free or substantially free of bubbles. The copolymer may also be present in the hydrogel in an amount sufficient to provide a viscosity of from about 1,000 cP to about 100,000 cP. For example, the copolymer may be present in the hydrogel in an amount sufficient to provide a viscosity of from about 1,000 cP, about 5,000 cP, about 10,000 cP, or about 20,000 cP to about 30,000 cP, about 40,000 cP, about 50,000 cP, about 75,000 cP, about 90,000 cP, or about 100,000 cP.

The polymeric center block of the copolymer may be a biodegradable polymer, thereby improving or increasing biodegradability of the solid, aqueous electrolyte composition. The biodegradable polymer of the polymeric center block is preferably naturally occurring. The polymeric center block may be or include, or be derived from, a polymer, such as a biodegradable polymer, including at least two free hydroxyl groups available for reaction with ε-caprolactone. As further described herein, the polymer including the at least two free hydroxyl groups may be reacted with ε-caprolactone to form the copolymer. Illustrative polymers including at least two free hydroxyl groups that may be utilized to form the polymeric center block (CB) may be or include, but are not limited to, one or more of polyvinyl alcohol (PVA), a hydroxyl-bearing polysaccharide, a biodegradable polyester, a hydroxy fatty acid (e.g., castor oil), or the like, or combinations thereof. Illustrative hydroxyl-bearing polysaccharides may be or include, but are not limited to, starch, cellulose, carboxymethyl cellulose, methyl cellulose, hydroxyethyl cellulose, chitin, guar gum, xanthan gum, agar-agar, pullulan, amylose, alginic acid, dextran, or the like, or combinations thereof. Illustrative biodegradable polyesters may be or include, but are not limited to, polylactide, polyglycolic acid, polylactide-co-glycolic acid, polyitaconic acid, polybutylene succinate, or the like, or combinations thereof. In a preferred embodiment, the polymer center block may be or include one or more of polyvinyl alcohol (PVA), a hydroxyl-bearing polysaccharide, a biodegradable polyester, or a hydroxy fatty acid.

In at least one embodiment, the polymeric center block of the copolymer may not be a biodegradable polymer. For example, the polymeric center block of the copolymer may be or include, but is not limited to, polyethylene glycol (PEG), hydroxy-terminated polyesters, hydroxyl-terminated polyolefins, such as hydroxy-terminated polybutadiene, or the like, or combinations thereof.

The copolymer, including at least two polycaprolactone (PCL) chains bonded to the polymeric center block, may be a graft copolymer or a block copolymer. Whether the copolymer is a graft copolymer or a block copolymer may be at least partially determined by the number and/or placement of the at least two free hydroxyl groups of the polymeric center block. For example, reacting ε-caprolactone with polymeric center blocks having the hydroxyl groups on monomers along a length of the polymeric center block chain forms graft copolymers. In another example, reacting ε-caprolactone with polymeric center blocks having each of the hydroxyl groups at respective ends of the polymeric center blocks forms block copolymers. Illustrative block copolymers may be or include triblock copolymers, tetrablock copolymers, star block copolymers, or combinations thereof.

As discussed above, the electrolyte composition may be a solid, aqueous electrolyte composition including the hydrogel of the copolymer and the salt dispersed in the hydrogel. The salt of the hydrogel may be or include any suitable ionic salt known in the art. Illustrative ionic salts may be or include, but are not limited to, one or more of organic-based salts, inorganic-based salts, room temperature ionic liquids, deep eutectic solvent-based salts, or the like, or combinations or mixtures thereof. In a preferred embodiment, the salts are or include salts useable in zinc/manganese (IV) oxide ($Zn/MnO_2$) electrochemistry. Illustrative salts may be or include, but are not limited to, zinc chloride ($ZnCl_2$), ammonium chloride ($NH_4Cl$), sodium chloride (NaCl), phosphate-buffered saline (PBS), sodium sulfate ($Na_2SO_4$), zinc sulfate ($ZnSO_4$), manganese sulfate ($MnSO_4$), magnesium chloride ($MgCl_2$), calcium chloride ($CaCl_2$), ferric chloride ($FeCl_3$), lithium hexafluorophosphate ($LiPF_6$), potassium hydroxide (KOH), sodium hydroxide (NaOH), or the like, or combinations thereof. In a preferred embodiment, the salt of the electrolyte composition may be or include ammonium chloride ($NH_4Cl$), zinc chloride ($ZnCl_2$), or a combination or mixture thereof. In another embodiment, the salt may be or include alkali metal salts, such as sodium hydroxide (NaOH), ammonium hydroxide ($NH_4OH$), potassium hydroxide (KOH), or combinations or mixtures thereof.

The salt may be present in an amount capable of, configured to, or sufficient to provide ionic conductivity. For example, the salt may be present in the hydrogel in an amount or concentration of at least 0.1M, more preferably at least 0.5M, even more preferably at least 2M, even more preferably at least 4M. The salt may be present in the hydrogel at a concentration of 10M or less, more preferably 6M or less. In another example, the salt may be present in the hydrogel in an amount of from about 3M to about 10M, about 4M to about 10M, about 5M to about 9M, or about 6M to about 8M. In an exemplary implementation, the salts included ammonium chloride and zinc chloride, where ammonium chloride is present in an amount of from about 2.5M to about 3M, about 2.8M to about 2.9M. or about 2.89M. and where zinc chloride is present in an amount of from about 0.5M to 1.5M, about 0.8M to about 1.2M. or about 0.9M.

In at least one embodiment, the electrolyte composition may include one or more additives. The one or more additives may be or include, but are not limited to, biodegradable or environmentally friendly nanomaterials. The biodegradable nanomaterials may be capable of or configured to provide and/or improve structural strength of the electrolyte layer or the electrolyte composition thereof without sacrificing flexibility of the electrolyte layer or the electrolyte composition thereof. Illustrative biodegradable nanomaterials of the additives may be or include, but are not limited to, polysaccharide-based nanomaterials, inorganic nanomaterials, or the like, or combinations thereof. Illustrative polysaccharide-based nanomaterials may be or include, but are not limited to, one or more of cellulose nanocrystals, chitin nanocrystals, chitosan nanocrystals, starch nanocrystals or the like, or combinations or mixtures thereof. Illustrative inorganic nanomaterials may be or include, but are not limited to, one or more of silicon oxides (e.g., fumed silica), aluminum oxides, layered silicates or lime, or combinations or mixtures thereof. Illustrative layered silicates may be or include, but are not limited to, one or more of bentonite, kaolinite, dickite, nacrite, stapulgite, illite, halloysite, montmorillonite, hectorite, fluorohectorite, nontronite, beidellite, saponite, volkonskoite, magadiite, medmontite, kenyaite, sauconite, muscovite, vermiculite, mica, hydromica, phegite, brammalite, celadonite, or combinations or mixtures thereof.

The one or more additives may be present in an amount of from at least 0.1 weight %, based on a total weight of the hydrogel. For example, the one or more additive may be present in an amount of at least 0.1 weight %, at least 0.5 weight %, or at least 1 weight %, based on a total weight of the hydrogel. The one or more additives may also be present in an amount of 40 weight % or less, based on a total weight of the hydrogel. For example, the one or more additives may be present in an amount of 40 weight % or less, 20 weight % or less, or 10 weight % or less, based on a total weight of the hydrogel.

In at least one embodiment, the electrolyte composition may include an aqueous solvent. For example, the electrolyte composition may include water. In at least one embodiment, the electrolyte composition may include a co-solvent. For example, the electrolyte composition may include water and an additional solvent. Illustrative co-solvents may be or include, but are not limited to, one or more of ethylene glycol, propylene glycol, diethylene glycol, dipropylene glycol, or combinations thereof. The cosolvent may include water in an amount greater than about 20%, greater than about 30%, greater than about 40%, greater than about 50% to greater than about 60%, greater than about 70%, greater than about 80%, greater than about 85%, or greater than about 90%, by total weight or volume of the aqueous solvent of the electrolyte composition.

In at least one embodiment, the electrolyte composition includes the hydrogel of the copolymer and the salt dispersed in the hydrogel, a solvent (e.g., water or water and a co-solvent), one or more photoinitiators, the optional one or more additives, or combinations thereof. For example, the electrolyte composition includes the hydrogel of the copolymer, the salt dispersed in the hydrogel, the solvent, the one or more additives, or combinations or mixtures thereof. In at least one embodiment, the electrolyte composition consists of or consists essentially of the hydrogel of the copolymer, the salt dispersed in the hydrogel, and the solvent (e.g., water or water and a cosolvent). In another embodiment, the electrolyte composition consists of or consists essentially of the hydrogel of the copolymer, the salt dispersed in the hydrogel, the solvent, and the one or more additives. The solvent, which may be water or a combination of water and a cosolvent, may provide the balance of the hydrogel. Suitable electrolyte compositions and processes and procedures for producing the same are disclosed in International Application No. PCT/US2020/046932, the disclosure of which is hereby incorporated herein by reference in its entirety.

As previously discussed, the electrolyte layer 112, 212 of the respective biodegradable electrochemical devices 100, 200 may be or include the solid, aqueous electrolyte composition. The solid, aqueous electrolyte composition may have sufficient mechanical and electrochemical properties necessary for a commercial printed battery or a commercially useful printed battery. For example, the solid, aqueous electrolyte composition may have a Young's modulus or storage modulus of greater than about 0.10 Megapascals (MPa), greater than about 0.15 MPa, or greater than about 0.20 MPa, thereby providing the solid, aqueous electrolyte composition with sufficient strength while maintaining sufficient flexibility to prevent breakage under stress. The solid, aqueous electrolyte composition may have a Young's modulus of less than or equal to about 100 MPa, less than or equal to about 80 MPa, less than or equal to about 60 MPa, or less.

As used herein, the term or expression "Yield strength" may refer to a maximum stress a material can experience or receive before the material begins to deform permanently. The solid, aqueous electrolyte composition may have a Yield strength of from about 5 kPa or greater. For example, the solid, aqueous electrolyte composition may have a Yield strength of from about 5 kPa or greater, about 8 kPa or greater, about 10 kPa or greater, about 12 kPa or greater, about 15 kPa or greater, or about 20 kPa or greater.

The solid, aqueous electrolyte composition may be electrochemically stable for both the anode active layers 108, 208 and cathode active layers 110, 210 of the respective biodegradable electrochemical devices 100, 200. For example, the solid, aqueous electrolyte composition may maintain a stable open circuit voltage over an extended period of time, thereby demonstrating electrochemical stability towards both the anode active layers 108, 208 and cathode active layers 110, 210 of the respective biodegradable electrochemical devices 100, 200. In at least one embodiment, the solid, aqueous electrolyte composition may be electrochemically stable in contact with the electrode layers for at least one month, at least two months, at least three months, at least four months, at least five months, at least six months, at least one year, or more.

The solid, aqueous electrolyte composition disclosed herein may be utilized in any electrochemical device, such as an electrochemical cell, a battery, and/or the biodegradable electrochemical devices 100, 200 disclosed herein. In a preferred embodiment, the solid, aqueous electrolyte composition may be utilized in a battery including a Zn anode active layer and a $MnO_2$ cathode active layer.

The current collectors 104, 106, 204, 206 of the respective biodegradable electrochemical devices 100, 200 may be capable of or configured to receive, conduct, and deliver electricity. Illustrative current collectors 104, 106, 204, 206 may be or include, but are not limited to, silver, such as silver microparticles and silver nanoparticles, carbon, such as carbon black, graphite, carbon fibers, carbon nanoparticles, such as carbon nanotubes, graphene, reduced graphene oxide (RGO), or the like, or any combination thereof.

Methods

Embodiments of the present disclosure may provide methods for fabricating an electrochemical device, such as the biodegradable electrochemical devices 100, 200 disclosed herein. The method may include providing a biodegradable substrate. The method may also include depositing an electrode and/or electrode composition adjacent or on the biodegradable substrate. Depositing the electrode may include depositing and drying a current collector of the electrode, and depositing and drying an active layer (i.e., anode or cathode material) adjacent or on the current collector. The method may also include drying the electrode and/or electrode composition. The electrode composition may be dried thermally (e.g., heating). The method may also include depositing a biodegradable, radiatively curable electrolyte composition on or adjacent the electrode composition. The method may further include radiatively curing the biodegradable radiatively curable electrolyte composition. The biodegradable radiatively curable electrolyte composition may be radiatively cured before or subsequent to drying the electrode composition. The biodegradable substrate may be thermally compatible with the optional thermal drying. For example, the biodegradable substrate may be dimensionally stable (e.g., no buckling and/or curling) when thermally drying. The method may include depositing a second electrode and/or electrode composition on or adjacent the biodegradable, radiatively curable electrolyte composition. In at least one embodiment, each of the first and second electrode compositions is a metal foil composition. The metal foil composition of the first electrode may be different from the metal foil composition of the second electrode.

In at least one embodiment, the electrochemical device, all of the components thereof, or substantially all of the components thereof are fabricated via a printing process. The printing process may include depositing, stamping, spraying, sputtering, jetting, coating, layering, or the like. For example, the one or more current collectors, the one or more electrode compositions, the biodegradable, radiatively curable electrolyte composition, or combinations thereof may be deposited via the printing process. Illustrative printing processes may be or include, but are not limited to, one or more of screen printing, inkjet printing, flexography printing (e.g. stamps), gravure printing, off-set printing, airbrushing, aerosol printing, typesetting, roll-to-roll methods, or the like, or combinations thereof. In a preferred embodiment, the components of the electrochemical device are printed via screen printing.

In at least one embodiment, radiatively curing the biodegradable radiatively curable electrolyte composition includes exposing the electrolyte composition to a radiant energy. The radiant energy may be ultraviolet light. Exposing the biodegradable radiatively curable electrolyte composition to the radiant energy may at least partially crosslink the biodegradable radiatively curable electrolyte composition, thereby forming a hydrogel. The biodegradable radiatively curable electrolyte composition may be radiatively cured at room temperature. In at least one embodiment, the biodegradable radiatively curable electrolyte composition is cured at an inert atmosphere. For example, the biodegradable radiatively curable electrolyte composition may be cured under nitrogen, argon, or the like. In another embodiment, the biodegradable radiatively curable electrolyte composition may be cured in a non-inert atmosphere.

In at least one embodiment, the biodegradable radiatively curable electrolyte composition may be radiatively cured in a period of time from about 5 ms to about 100 ms. For example, the biodegradable radiatively curable electrolyte composition may be radiatively cured in a period of time from about 5 ms, about about 10 ms, about 15 ms, about 20 ms, about 30 ms, about 40 ms, or about 50 ms to about 60 ms, about 70 ms, about 80 ms, about 85 ms, about 90 ms, about 95 ms, or about 100 ms. The period of time sufficient to radiatively cure the biodegradable radiatively curable electrolyte composition may be at least partially determined by a power output of the UV light.

In at least one embodiment, the method may also include depositing an adhesive, such as a biodegradable adhesive, to thereby provide the seals 116, 118, 216, 218 of the respective biodegradable electrochemical devices 100, 200. For example, the method may include depositing a layer of the adhesive to couple the substrates or part of the substrates (e.g., area around the tabs 124, 126, 224, 226), of the electrochemical device with one another. In some embodiments, the adhesive may be a hot-melt adhesive. In another embodiment, the electrochemical device may be free or substantially free from any adhesive. For example, the biodegradable substrate may be weldable and/or heat-sealable without the use of an additional adhesive.

In at least one embodiment, the biodegradable substrate may be a continuous web, or may be supported by a continuous web. As used herein, the term "web" may refer to a moving supporting surface, such as a conveyor belt. In at least one example, a plurality of electrochemical devices are simultaneously printed as independent or linked elements or components on the continuous web. For example, respective components of the plurality of electrochemical devices may be simultaneously printed as independent or linked components on the continuous web as an array in a parallel process. As used herein, the term or expression "linked elements" or "linked components" may refer to elements or components, respectively, of the electrochemical device that are physically touching, overlapping, or otherwise contacting one another. Illustrative linked elements may be or include an active layer (e.g., cathode active layer or anode active layer) disposed adjacent to or on top of a current collector layer, a current collector layer and a copper tape tab, or an electrolyte layer on top of an active cathode/anode layer.

In at least one embodiment of an exemplary biodegradable electrochemical device, the solid aqueous electrolytes thereof, and methods for synthesizing and fabricating the same are available, the layers of various materials, including current collectors, cathode/anode materials, binders, adhesives, and electrolyte need to be printed with high fidelity and accuracy. Furthermore, retention of moisture within the aqueous electrolyte is critical to battery performance via maintenance of solubilized salts for good ion conductivity and printed biodegradable or compostable batteries such as these suffer from shortened lifespan due to water losses via evaporation through the biodegradable substrate, which may be a polylactic acid (PLA) film. Such electrochemical devices may have biodegradable polymeric composite film enclosure pouches that have a biodegradable barrier layer. Illustrative biodegradable enclosure materials may be or include, but are not limited to, one or more of polylactic acid (PLA), polylactic-co-glycolic acid (PLGA), silk-fibroin, chitosan, polycaprolactone (PCL), polyhydroxy butyrate (PHB), rice paper, cellulose, or combinations or composites thereof.

In at least one embodiment, flexible biodegradable electrochemical devices including an anode, a cathode and an electrolyte composition comprising a crosslinked, biodegradable polymeric material that is radiatively curable prior to being crosslinked, printed between the anode and the cathode, may have biodegradable moisture or water vapor barriers or barrier layers forming an enclosure, film or pouch around the external portion of an electrochemical device to prevent moisture present within the aqueous electrolyte materials from evaporating. In such embodiments, since the entire electrochemical device is biodegradable, the device may have prolonged service life due to the improved water vapor barrier or moisture barrier layer properties of the enclosure pouch and be biodegradable and/or biodegradable once its service life is over. The function of the biodegradable water vapor barrier or enclosure is to provide a moisture barrier layer to impede the evaporation of water from aqueous electrolyte compositions within the electrochemical device, thus extending service life of the electrochemical device. It should be noted, in reference to water vapor barriers or moisture barrier layers described herein, that while certain embodiments of electrochemical devices may have a substantial amount of water or moisture, that other solvents or evaporable materials may also be conducive to prolonged and acceptable operation of an electrochemical device enclosed within water vapor barriers of the present disclosure.

The biodegradable water vapor barrier of the respective biodegradable electrochemical devices may be stable at temperatures of from about 50° C. to about 150° C. As used herein, the term "stable" or "stability" may refer to the ability of the substrate to resist dimensional changes and maintain structural integrity when exposed to temperature of from about 50° C. to about 150° C. For example, the biodegradable water vapor barrier may be capable of or configured to maintain structural integrity with dimensional changes of less than about 20%, less than about 15%, or less than about 10% after exposure to temperatures of from about 50° C. to about 150° C. In one example, each of the biodegradable water vapor barriers may be stable (e.g., dimensional changes less than 20%) at a temperature of from about 50° C., about 60° C., about 70° C. about 80° C. about 90° C. about 100° C. or about 110° C. to about 120° C. about 130° C. about 140° C. or about 150° C. In another example, each of the biodegradable water vapor barriers may be stable at a temperature of at least 100° C. at least 105° C. at least 110° C. at least 115° C. at least 120° C. at least 125° C. at least 130° C. at least 135° C. at least 140° ° C. or at least 145° C. In at least one embodiment, the biodegradable water vapor barriers may be stable at temperatures of from about 50° C. to about 150° C. for a period of from about 5 min to about 60) min or greater. For example, the biodegradable water vapor barriers may be stable at the aforementioned temperatures for a period of time of from about 5 min. about 10 min. about 20 min. or about 30 min to about 40 min, about 45 min. about 50 min. about 60 min. or greater.

In at least one embodiment, the biodegradable water vapor barrier material is weldable, bondable, and/or permanently thermo-sealable without the use of an additional adhesive. For example, the biodegradable water vapor barriers described herein for electrochemical device enclosures may be weldable and/or bondable with one another without the use of the respective seals. Illustrative biodegradable water vapor barrier materials that may be weldable and/or bondable with one another may be or include, but are not limited to, thermoplastics, such as polylactic acid (PLA), polylactides modified with a nucleating agent to enhance crystallinity, such as polylactide modified with nucleating agent D (PLA-D) and polylactide modified with nucleating agent E (PLA-E), polybutylene succinate (PBS), polybutylene adipate terephthalate (PBAT), blends of PLA and polyhydroxy butyrate (PHB), PHB-based blends, or the like, or combinations thereof. As used herein, the term or expression "bondable," "weldable," and/or "permanently thermo-sealable" may refer to an ability of a material (e.g., substrate) to heat seal two surfaces with one another or permanently join two surfaces with one another via heating or melting.

In some embodiments, the biodegradable enclosures, pouches, or water vapor barriers may be made from metallized, biodegradable polylactic acid (PLA) film, such as an aluminum metalized polylactic acid film. The metal surface layer providing the metallization may be aluminum. In certain embodiments, the metallization layer may include aluminum, other suitable metals or alloys, ceramics, clays, hybrid materials of inorganic-organic biopolymers, and combinations thereof. Alternative embodiments may have multiple layers of metal, metal on an inner layer of a multilayer film, an outer layer, or both. The PLA film may be biaxially oriented to improve physical properties of the enclosure pouch. Still other embodiments may have additives incorporated into the film, providing enhanced moisture barrier properties. Biodegradable enclosures, pouches, or water vapor barriers for electrochemical devices may have single layer, or multiple layers with combinations of one or more materials in alternate embodiments. Metalized layer films or barriers can provide a thickness of from about 1 nm to about 100 nm, from about 5 nm to about 50 nm, or from about 10 nm to about 40 nm. Single layer films or barriers in certain examples may have an overall thickness from about 1 μm to about 100 μm, from about 40 μm to about 80 μm, or from about 50 μm to about 75 μm. Metallized layers of water vapor barriers may have a thickness from about 0.5 nm to about 100 nm, from about 5 nm to about 50 nm, or from about 5 nm to about 25 nm over a base film layer such as PLA.

In certain examples, a biodegradable enclosure, pouch, or water vapor barrier may be made of a multilayer composite constructed by either extruding or laminating a biodegradable polymer on each side of a thin metal foil, such as aluminum. In contrast to a metallized polymer layer in a biodegradable enclosure, a thin and continuous metal layer within such a multilayered laminated composite can provide a robust barrier layer coupled with one or more biodegradable enclosure layers. An advantage of such a multilayered laminated structure is that the continuous metal film forms a layer that can more effectively prevent water permeation through the composite, as well as providing an option to provide thicker metal or aluminum layers or multiple metal layers. Thus, a metal layer providing water vapor barrier can be from about 1 μm to about 200 μm, or from about 5 μm to about 150 μm, or from about 10 μm to about 100 μm. Metal foil layers in accordance with the present disclosure are not as prone to issues such as pinholes in the aluminum or metal layer, which can be more prevalent in metal films formed from sputtering or other deposition methods as described herein. The presence of pinholes in metal layers or other barrier layers within a biodegradable enclosure, pouch, or water vapor barrier can in some instances allow some water permeation through the composite material.

For certain examples having multilayer composites according to the present disclosure, several methods may be used to form these multilayer laminates. In a first example, pre-existing polymer sheets can be pressed at a suitable temperature and pressure on one side or each side of an aluminum sheet, with the use of one or more interdigitated or interspersed adhesive tie layers to enable or enhance the adhesion of the polymer sheet with the aluminum or metal foil. In a second example, the polymer layer and adhesive tie layers can be directly melt-extruded as thin films onto the surface of an aluminum or other metal foil, using multilayer film casting processes, known to one skilled in the art. Additional metal foils or films incorporating metals such as magnesium, titanium, iron, nickel, copper, zinc, or alloys or mixtures thereof may be used in accordance with the present disclosure.

In certain embodiments, other materials known to have water vapor barrier properties may be used. These materials must conform to the biodegradable and/or compostable format and include materials such as beeswax, plasticizers, and alternative biodegradable polymer composite films. In alternate embodiments wherein the water vapor barrier is not a part of the substrate of the electrochemical device, water vapor barriers may be used having higher temperature stability and resistance as compared to biodegradable materials, polymers or composites, having wider ranges of temperature resistance. Embodiments of electrochemical devices having biodegradable enclosures or water vapor barriers having moisture barrier properties may exhibit reduced water vapor transmission rates (WVTR) as compared to electrochemical devices without such barriers, layers, or enclosures, exhibiting WVTR of from about 0% over 24 hour to about 5% over 24 hour, from about 0.1% over 24 hour to about 2% over 24 hour, or from about 0.5% over 24 hour to about 1% over 24 hour. WVTR may also be expressed as a percentage of total weight of water lost as compared to a total weight of the electrochemical device including the enclosure or moisture barrier. Embodiments of electrochemical devices having biodegradable enclosures or water vapor barriers having moisture barrier properties in accordance with the present disclosure may exhibit reduced water vapor transmission rates (WVTR) as compared to electrochemical devices without such barrier layers or enclosures, the water vapor barrier exhibiting WVTR of from about 0.0 $g/m^2/24$ hour to about 10 $g/m^2/24$ hour, from about 0.5 $g/m^2/24$ hour to about 5 $g/m^2/24$ hour, or from about 1 $g/m^2/24$ hour to about 2 $g/m^2/24$ hour. Expressions of WVTR are provided herein as weight percent, or wt % of the total electrochemical device. Certain examples of electrochemical devices having biodegradable enclosures or water vapor barriers having moisture barrier properties may exhibit reduced water vapor transmission rates (WVTR) as compared to electrochemical devices without such barrier layers or enclosures, the water vapor barriers of the present disclosure exhibiting WVTR of from about 0 $mg/cm^2/24$ hour to about 5.0 $mg/cm^2/24$ hour, from about 0.1 $mg/cm^2/24$ hour to about 1 $mg/cm^2/24$ hour, or from about 0.1 $mg/cm^2/24$ hour to about 0.5 $mg/cm^2/24$ hour.

In some embodiments, the electrochemical device may be arranged such that a battery or electrochemical device is contained in an enclosure or entirely within a water vapor barrier as described having improved water vapor barrier properties and oriented or arranged such that the cathode and anode are in a side-by-side or lateral X-Y plane geometry, as illustrated in FIG. 1. In alternate embodiments, the electrochemical device may be arranged such that a battery or electrochemical device is contained in an enclosure as described having improved water vapor barrier properties and oriented or arranged such that the cathode and anode are in a stacked geometry, as illustrated in FIG. 2.

Embodiments of the present disclosure may provide methods for fabricating, producing, or otherwise enclosing an electrochemical device having improved moisture barrier properties or water vapor barrier properties. The method may include orienting a first metalized PLA film having four edges and a second metalized PLA film having four edges such that a non-metalized side of the first metalized PLA film is facing a non-metalized side of the second metalized PLA film. One or more edges of the first and second metallized PLA films may be sealed together. A biodegradable or compostable electrochemical device may be placed between the first metalized PLA film and the second metalized PLA film, followed by sealing the edges of the first metalized PLA film and the edges of the second metalized PLA film together, such that one or more electrodes of the electrochemical device are exposed through at least one of four edges.

The method may alternatively include steps to orient a first metalized PLA film having four edges on a top side of an electrochemical device such that a non-metalized side is facing the electrochemical device. A second metalized PLA film is oriented on a bottom side of an electrochemical device such that a non-metalized side is facing the electrochemical device. All four edges of the first metalized PLA film and the four edges of the second metalized PLA film may be sealed together, such that the one or more electrodes are exposed through at least one of four edges. Enclosures or water vapor barriers fabricated in this manner from biodegradable aluminized polymer barrier layers in combination with surface coatings and/or polymer additives may reduce or prevent water vapor loss from a biodegradable or compostable electrochemical device. Such devices may significantly extend the service life of biodegradable or compostable electrochemical devices by preventing the electrolyte solvent from evaporating over time.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Comparative Example 1

Figure 3:
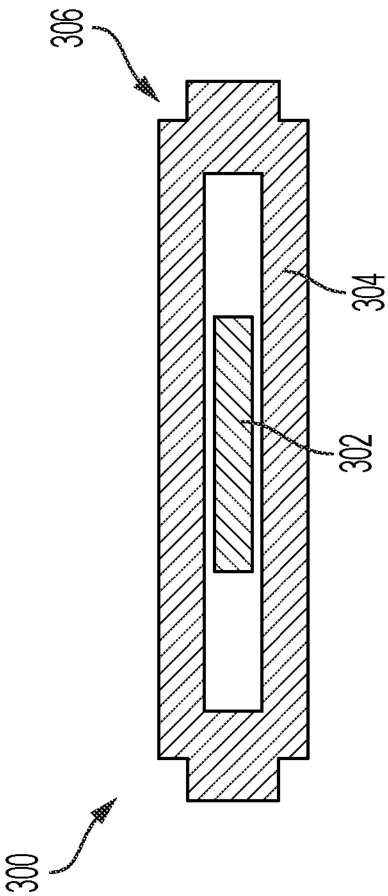
FIG. 3 illustrates a cross-sectional view of a comparative example of a fully assembled surrogate for a biodegradable battery assembly having a water vapor barrier, according to one or more embodiments.

A surrogate test related to embodiments described herein of a biodegradable battery configuration having improved moisture retention is described in relation to Comparative Example 1. FIG. 3 illustrates a cross-sectional view of a comparative example of a fully assembled surrogate for a biodegradable battery assembly having a water vapor barrier, according to one or more embodiments. This surrogate test was performed to measure the water loss through PLA-D biodegradable substrate within a similar context to a fully assembled biodegradable battery. Comparative Example 1 is a surrogate battery assembly 300 with film enclosure 304 surrounding a patch of filter paper 302 as a surrogate for an aqueous electrolyte battery composition. Two sheets of 80 μm thick PLA-D bi-axially stretched films were cut into 2 cm×3 cm squares. Two of the cut films were stacked together with similar orientation. An MSK-130 heat sealer from MTI corporation set at 170° C. for 5 seconds was used to heat seal three of the four edges of the film sheets together, resulting in a pouch or enclosure with a single, 3 cm unsealed side. A 1 cm square patch of whatman 1825-150 filter paper 302 was placed into the 2 cm×3 cm pouch 304. The pouch with the filter paper 302 inside was then weighed and tared. 3 drops of DI water were added to the paper in the pouch and then the remaining open edge of the pouch was sealed, forming a heat sealed edge 306 under the same conditions as mentioned previously. The weight of the pouch was measured over time to determine the loss of water. The surrogate test includes the creation of a full sized, sealed substrate configuration, with known, measured amounts of water added to reflect similar amounts found in fully assembled biodegradable batteries. The water loss over time is then measured by periodically weighing the surrogate battery assembly 300. This testing protocol is then repeated with experimental Examples 1-3, to evaluate various embodiments of film enclosures to inhibit water transmission loss from aqueous based electrolyte compositions within biodegradable electrochemical devices.

Example 1

Figure 4:
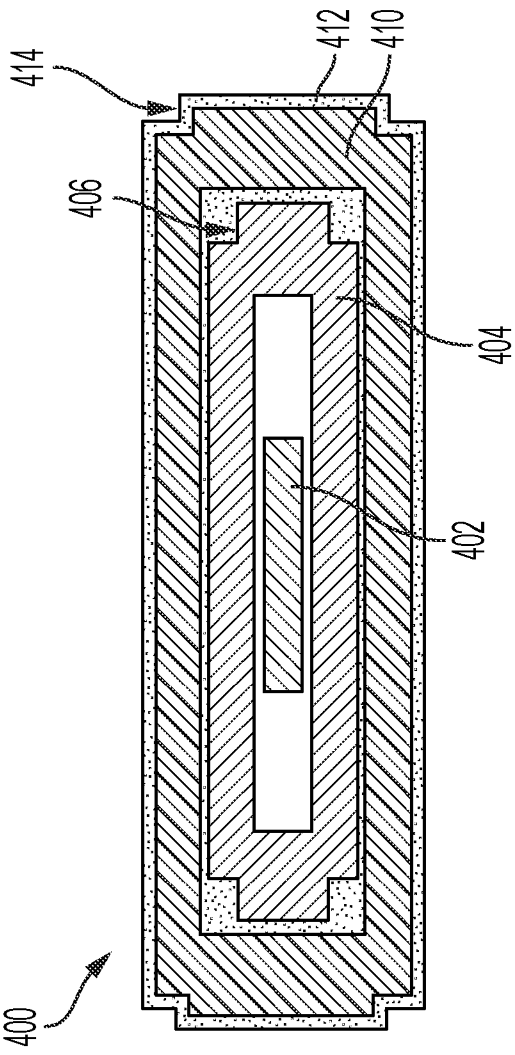
FIG. 4 illustrates a cross-sectional view of the embodiment of a fully assembled surrogate for an electrochemical device assembly of Example 1, having a water vapor barrier, according to one or more embodiments.

FIG. 4 illustrates a cross-sectional view of the embodiment of a fully assembled surrogate for an electrochemical device assembly of Example 1, having a water vapor barrier, according to one or more embodiments. Two 4 cm×4 cm square sheets of Enviromet HS 75 μm thick Aluminized PLA manufactured by Celplast, Toronto Ontario, Canada, were oriented and stacked together such that the PLA side was facing inward to form an enclosure 400 for an electrochemical device. An MSK-130 heat sealer with a soft die set at 170° C. for 3 seconds was used to seal three of the four edges of the sheet together to make an enclosure pouch 400 with one open side, resulting in an enclosure pouch 400 having an internal PLA layer 410 and an external aluminum layer 412. A water-soaked filter paper 402 and PLA-D enclosure pouch 404 sealed at an edge similar to the embodiment described in regard to Comparative Example 1 was then placed inside of the PLA-Al pouch 400 and the remaining edge 414 was sealed using the MSK-130. The weight of the pouch 400 was measured over time to determine the loss of water.

Example 2

Figure 5:
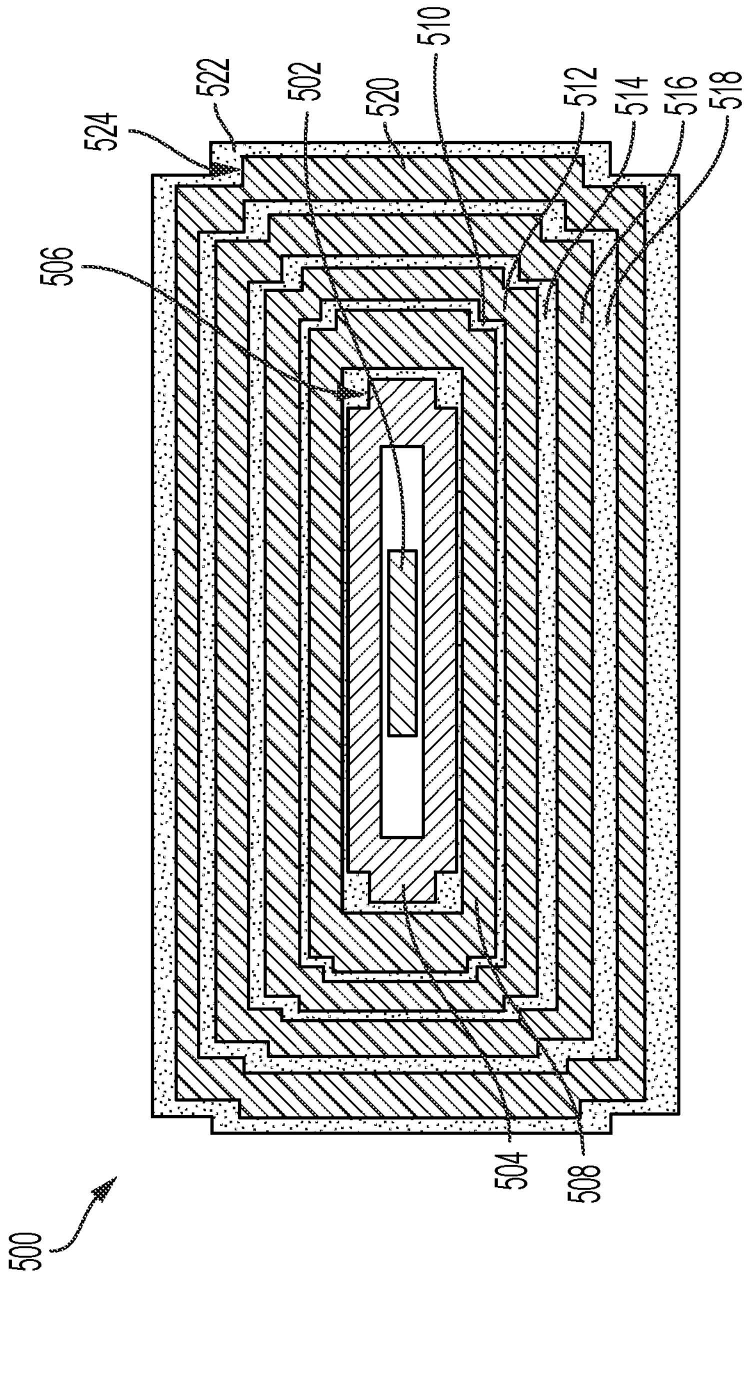
FIG. 5 illustrates a cross-sectional view of the embodiment of a fully assembled surrogate for an electrochemical device assembly of Example 2, having a water vapor barrier, according to one or more embodiments.

FIG. 5 illustrates a cross-sectional view of the embodiment of a fully assembled surrogate for an electrochemical device assembly of Example 2, having a water vapor barrier, according to one or more embodiments. Eight 4 cm×4 cm square sheets of Enviromet 75 μm thick Aluminized PLA were oriented and stacked together such that the PLA side was facing inward to form an enclosure pouch or water vapor barrier 500 having four layers for an electrochemical device. An MSK-130 heat sealer with a soft die set at 170° C. for 3 seconds was used to seal three of the four edges of each sheet together to make an enclosure pouch 500 with one open side. In this embodiment, the enclosure pouch 500 walls consist of a first layer having a first PLA layer 508 and a first aluminum layer 510, a second layer having a second PLA layer 512 and a second aluminum layer 514, a third layer having a third PLA layer 516 and a third aluminum layer 518, and a fourth layer having a fourth PLA layer 520 and a fourth aluminum layer 522, resulting in four stacked sheets of Enviromet Aluminized PLA. A water-soaked filter paper 502 and PLA-D enclosure pouch 504 sealed at an edge 506 similar to the embodiment described in regard to Comparative Example 1 was then placed inside of the PLA-Al pouch 500 and the remaining edge 522 was sealed using the MSK-130. The weight of the enclosure pouch 500 was measured over time to determine the loss of water.

Example 3

Figure 6:
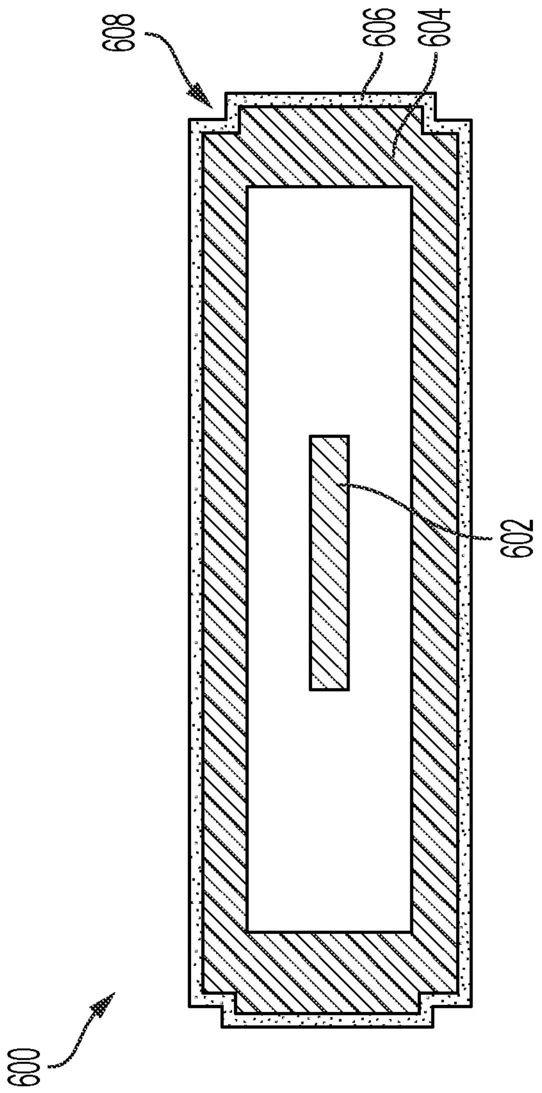
FIG. 6 illustrates a cross-sectional view of the embodiment of a fully assembled surrogate for an electrochemical device assembly of Example 3, having a water vapor barrier, according to one or more embodiments.

FIG. 6 illustrates a cross-sectional view of the embodiment of a fully assembled surrogate for an electrochemical device assembly of Example 3, having a water vapor barrier, according to one or more embodiments. Two 4 cm×4 cm square sheets of Enviromet 75 μm thick Aluminized PLA were oriented and stacked together such that the PLA side was facing inward to form an enclosure pouch 600 having a single water vapor barrier layer for an electrochemical device. An MSK-130 heat sealer with a soft die set at 170 C for 3 seconds was used to seal 3 of the 4 edges together to make an enclosure pouch 600 with one open side. In this embodiment, the enclosure pouch 600 walls consists of a PLA layer 604 and an aluminum layer 606. A 1 cm square patch of Whatman 1825-150 filter paper 602 was placed into the 4 cm×4 cm enclosure pouch 600. The pouch 600 with the paper patch 602 inside was then weighed and tared. 3 drops of DI water were added to the paper 602 in the pouch 600 and then last open edge of the pouch was sealed as before with the MSK-130. The weight of the pouch was measured over time to determine the loss of water.

Examples 4, 5, 6, and 7

Figure 7:
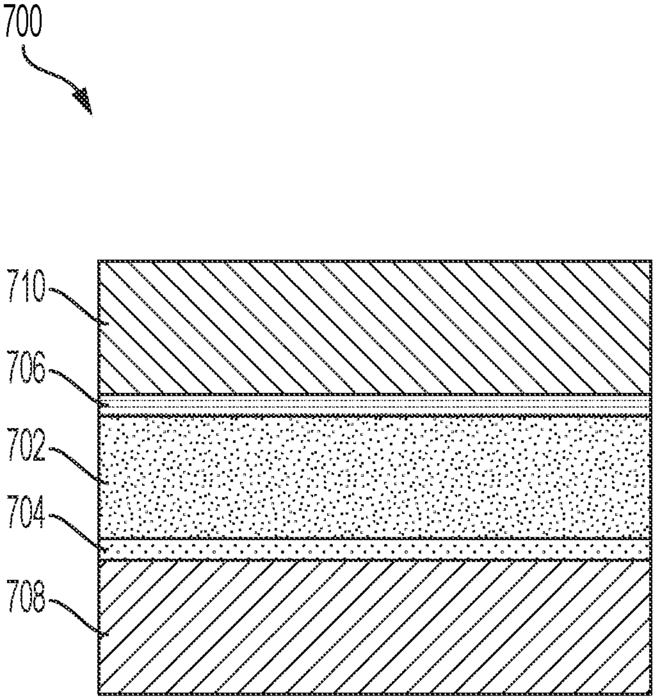
FIG. 7 illustrates a cross-sectional view of an example of a surrogate for an electrochemical device assembly having a multilaminate enclosure structure, in accordance with the present disclosure.

FIG. 7 illustrates a cross-sectional view of an example of a surrogate for an electrochemical device assembly having a multilaminate enclosure structure, in accordance with the present disclosure. In the multilayer enclosure structure 700 a first side and a second side of a metal barrier layer 702 have a first adhesive tie layer 704 and a second adhesive tie layer 706 disposed onto the metal barrier layer 702. It should be noted that in certain materials configurations for a multilayer composite structures 700, no adhesive tie layers are needed, but in other examples, in instances where a polymer will not adhere to an aluminum or other metal surface without an adhesive, the presence of an adhesive tie layer can be desirable. In certain examples, the composition of the adhesive tie layers 704, 706 is biodegradable, however, as they are sufficiently thin compared to the metal and polymer layers, they may be fabricated partially or fully of non-biodegradable material. In such examples, the relative weight percentage of any non-biodegradable material would be less than 10% by weight of the entire enclosure material. In certain examples, the aluminum or metal barrier 702 surface may have a surface treatment that can enhance the adhesion of one or more layers to a surface of the metal barrier layer 702, such as a plasma or corona treatment. It is expected that both of the external first biodegradable polymer layer 708 and a second biodegradable polymer layer 710 will be constructed of the same material, however, in certain examples the first biodegradable polymer layer 708 and the second biodegradable polymer layer 710 may not be constructed of the same material and therefore the material composition of adhesive tie layers 704, 706 could differ as well, as would be required to optimize the adhesion with each polymer type used in the first biodegradable polymer layer 708 and the second biodegradable polymer layer 710. Metal layers or metal barrier layers as described herein provide multilayer enclosure structures of the present disclosure with a moisture impermeable layer, or moisture impenetrable layer. In certain examples of such multilayer enclosure structures, the metal layer or metal barrier layer can allow for no water, moisture, or solvent to pass through the enclosure.

Example 4: production of a half-structure multilayer composite using a commercial tri-layer PLA thin film as a tie layer. A PLA sheet of approximately 100 μm thick was obtained by melt-extruding a formulation of a commercial extrusion grade PLA, obtained from Corbion, blended with a crystallization agent (agent D, Luminy D070 by Corbion). A multilayer stack was prepared using a 40 μm thick aluminum foil, obtained from All Foils Inc., Ohio, USA, a sheet of the extruded PLA-D polymer and as an in-between adhesive tie layer, a tri-layer PLA thin film, Evlon EV-HS1 The multilayer stack was pressed at 120° C. under 5000 PSI for 20 minutes. The resulting multilayer film can be considered as half the multilayer structure detailed in FIG. 7. However, since the aluminum layer is acting as a water vapor barrier layer, this half-structure is sufficient to demonstrate the barrier properties in surrogate evaluation in accordance with the present disclosure. The complete structure may only be needed in certain examples to protect the aluminum layer from being mechanically damaged by adding a polymer scratch-resistant layer. The complete structure can be fabricated using the same method as the half structure.

Example 5: production of a half-structure multilayer composite using a non-biodegradable polyamide-based adhesive as a tie layer. A 40 μm thick aluminum foil was coated with a thin layer of polyamide-based adhesive powder (Evonik Vestamelt Hylink) using an electrostatic spray gun, then placed in an oven at 140° C. for 10 minutes. A PLA-D sheet obtained as detailed in Example 4 was then applied to the adhesive tie layer side of the aluminum foil and pressed at 120° C. under 5000 PSI for 20 minutes. The adhesive tie layer weights 2 $mg/cm^2$ whereas the half structure weights 32.4 $mg/cm^2$, making the adhesive tie layer weight approximately 6 wt % based on a total weight of the half structure. It can be calculated that the adhesive tie layer weight of a full symmetric multilaminate structure would be 4 $mg/cm^2$ out of 54.4 $mg/cm^2$ or 7.4 wt % of non-biodegradable adhesive tie layer.

Example 6: production of a half-structure multilayer composite using a thin film of polycaprolactone (PCL) as an adhesive tie layer. A thin film of a PCL adhesive tie layer was obtained by pressing CAPA6500 PCL pellets, obtained from Ingevity, at 100° C. under 5000 PSI for 20 min. A multilayer stack was prepared using a 40 μm thick aluminum foil, a sheet of extruded PLA-D, as used in Example 4 and in accordance with the present disclosure, and PCL thin film as an adhesive tie-layer. The multilayer stack was pressed at 120° C. under 5000 PSI for 20 minutes.

Example 7: production of a half-structure multilayer composite using a thin film of an amorphous grade of PLA as an adhesive tie layer. A thin film of amorphous PLA layer was produced by pressing PLA pellets at 200° C. under 5000 PSI for 20 min. A multilayer stack was prepared using a 40 μm thick aluminum foil, a sheet of extruded PLA-D (as in Example 4) and as an interdigitated amorphous PLA thin film as an adhesive tie layer. The multilayer stack was pressed at 120° C. under 5000 PSI for 20 minutes.

In certain embodiments, the multilayer composites from Examples 6 and 7 can be produced in a single-step by directly melt-extruding a dual layer of adhesive tie layer and PLA film on to of an aluminum roll, as commonly performed by the multilayer packaging manufacturing industry.

To demonstrate the barrier properties of the multilayer composites produced in Examples 4, 5, 6 and 7, hermetically sealed pouches of each multilayer laminate (half structures) were prepared by cutting sheets of similar dimensions and thermally sealing their edges by pressing them between the jaws of a hand-held thermal sealer set at 200° C. for 5 seconds. Each pouch contained a paper tissue soaked with water. The weight of each pouch was then measured each day as a means to monitor the water permeation through the multilayer composites and subsequent evaporation.

Figure 8:
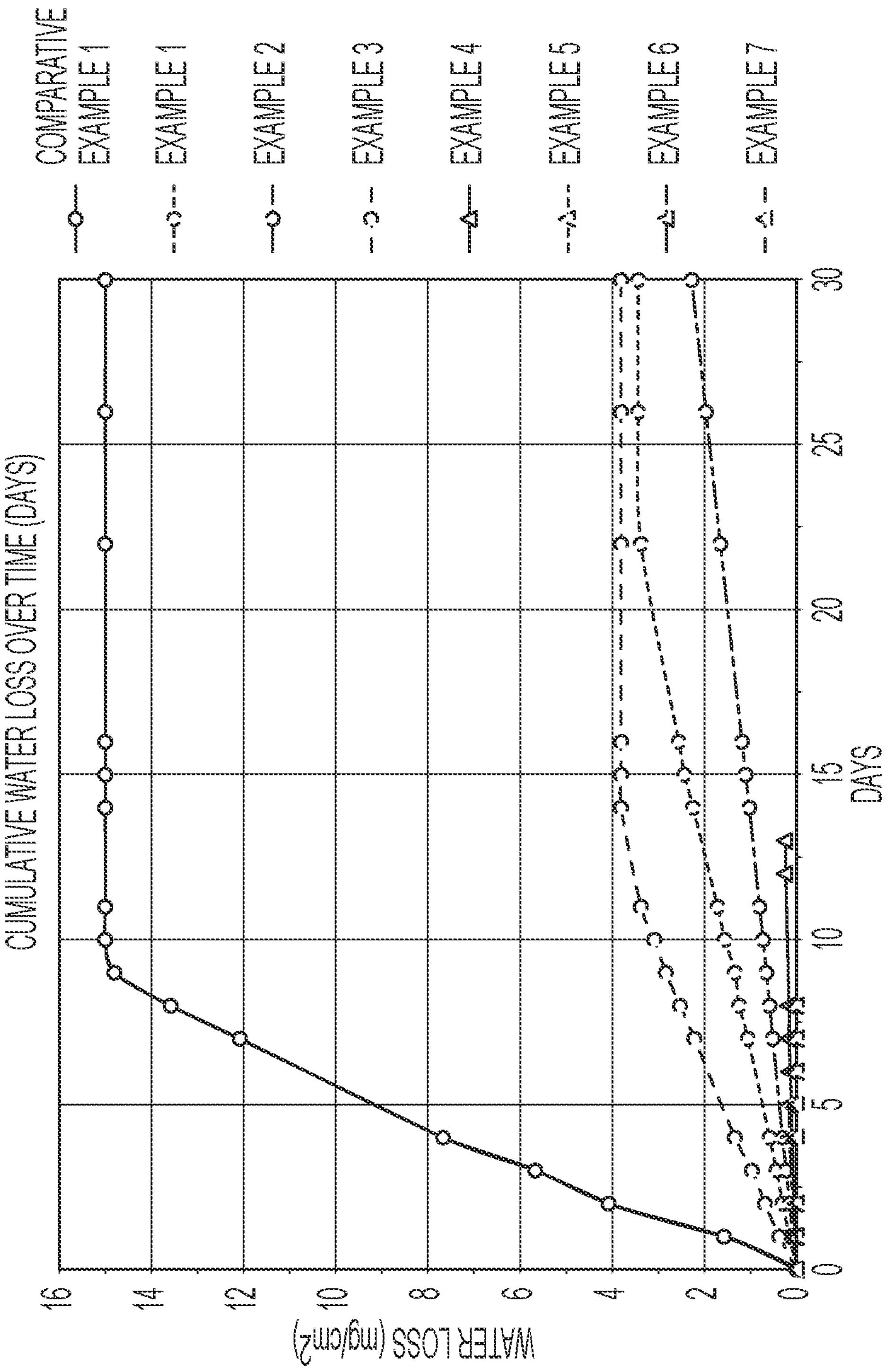
FIG. 8 illustrates a plot of water loss in milligrams per square centimeter vs. time in days for the comparative example of FIG. 3 compared to examples 1-5 of FIGS. 4, 5, 6, and 7, respectively.

FIG. 8 illustrates a plot of water loss in milligrams per square centimeter vs. time in day's for the Comparative Example of FIG. 3 compared to Examples 1 to 7 of FIGS. 4, 5, 6, and 7, respectively. The cumulative water loss in milligrams per square centimeter was measured by weight every 24 hrs for each example, normalized for surface area, and then plotted. Comparative Example 1, having only PLA-D substrate as a barrier layer shows a high cumulative water loss of ~15 mg/cm$^2$, exhibiting total loss of water by day 9. Example 1 with an extra aluminized PLA barrier layer shows a significantly reduced cumulative water loss of about 1.34 mg/cm$^2$ by day 9. Example 2 with four combined aluminized PLA barrier layers shows a significant reduction in cumulative water loss at 0.66 mg/cm$^2$ by day 9. Example 3 with only aluminized PLA as a barrier layer shows a moderately improved reduction in cumulative water loss of 2.84 mg/cm$^2$ on day 9 as compared to the total water loss of Comparative Example 1 at a similar time. The multilaminate samples of Examples 4, 5, 6, and 7 showed virtually no or negligible water loss by day 9. Full results are reported in Tables 1 and 2.

TABLE 1

| Time | COMPARATIVE EXAMPLE 1 | EXAMPLE 1 | EXAMPLE 2 | EXAMPLE 3 |
|---|---|---|---|---|
| | Water Loss | | | |
| (days) | mg/cm2 | mg/cm2 | mg/cm2 | mg/cm2 |
| 0 | 0 | 0 | 0 | 0 |
| 1 | 1.58 | 0.16 | 0.08 | 0.38 |
| 2 | 4.08 | 0.31 | 0.16 | 0.69 |
| 3 | 5.67 | 0.44 | 0.23 | 0.97 |
| 4 | 7.67 | 0.59 | 0.31 | 1.34 |
| 5 | — | — | — | — |
| 6 | — | — | — | — |
| 7 | 12.08 | 1.06 | 0.52 | 2.22 |
| 8 | 13.58 | 1.25 | 0.59 | 2.53 |
| 9 | 14.8 | 1.34 | 0.66 | 2.84 |
| 10 | 15 | 1.56 | 0.73 | 3.09 |
| 11 | 15 | 1.72 | 0.81 | 3.38 |
| 12 | — | — | — | — |
| 13 | — | — | — | — |
| 14 | 15 | 2.25 | 1.03 | 3.81 |
| 15 | 15 | 2.44 | 1.11 | 3.81 |
| 16 | 15 | 2.56 | 1.19 | 3.81 |
| 22 | 15 | 3.38 | 1.66 | 3.81 |
| 26 | 15 | 3.44 | 1.97 | 3.81 |
| 30 | 15 | 3.44 | 2.28 | 3.81 |

TABLE 2

| Time | EXAMPLE 4 | \|EXAMPLE 5 | EXAMPLE 6 | EXAMPLE 7 |
|---|---|---|---|---|
| | Water Loss | | | |
| (days) | mg/cm2 | mg/cm2 | mg/cm2 | mg/cm2 |
| 0 | 0 | 0 | 0 | 0 |
| 1 | 0.04 | 0 | — | — |
| 2 | — | 0 | — | — |
| 3 | — | — | — | — |
| 4 | — | — | 0.16 | 0 |
| 5 | 0.12 | — | 0.16 | 0 |
| 6 | 0.14 | 0 | 0.16 | — |
| 7 | 0.17 | 0 | — | — |
| 8 | 0.17 | 0 | — | — |
| 9 | — | — | — | — |
| 10 | — | — | — | — |
| 11 | — | — | 0.16 | 0 |
| 12 | 0.24 | — | 0.16 | 0 |
| 13 | 0.24 | 0 | — | — |
| 14 | 0.26 | 0 | — | — |
| 15 | — | — | — | — |
| 16 | — | — | — | — |
| 19 | 0.33 | — | — | — |
| 20 | 0.34 | — | — | — |
| 30 | — | — | — | — |

Continuity Testing

The utilization of embodiments of biodegradable batteries having barrier layers as described herein presents the possible issue of impacting the continuity of the battery tabs, particularly with the use of heat seal across the tabs. This was evaluated by assembling several full sized batteries using aluminized PLA as an external barrier layer, similar to Example 2. A lower temperature of 135° C. for the MSK sealer was used to prevent unnecessary heat exposure and potential damage to the battery tab while still providing a strong seal. The MSK sealer was set to the lower temperature of 135° C. in soft mode for a longer time of 6 seconds. The device was found to be fully functional with no loss of continuity across the tabs after the heat sealing.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. An electrochemical device comprising:

an anode;

a cathode;

an electrolyte composition disposed between the anode and the cathode; and a water vapor barrier comprising an enclosure pouch comprising a first metalized polylactic acid (PLA) film having a non-metalized side and a second metalized PLA film having a non-metalized side, wherein the non-metalized side of the first metalized PLA film faces the non-metalized side of the second metalized PLA film, and edge portions of the first and second metalized PLA films are sealed together to enclose the electrochemical device, and wherein the water vapor barrier is disposed to reduce water vapor escaping from the electrochemical device.

2. The electrochemical device of claim 1, wherein the water vapor barrier further comprises polylactic acid (PLA).

3. The electrochemical device of claim 1, wherein the first metalized PLA film or the second metalized PLA film comprises a metalized coating comprising magnesium, titanium, iron, nickel, copper, zinc, or combinations thereof.

4. The electrochemical device of claim 1, wherein the first metalized PLA film or the second metalized PLA film comprises a metalized coating comprising aluminum.

5. The electrochemical device of claim 1, wherein the water vapor barrier further comprises multiple layers.

6. The electrochemical device of claim 1, wherein the water vapor barrier further comprises a moisture impermeable layer.

7. The electrochemical device of claim 1, wherein the metalized coating comprises a metal layer having a thickness of from about 1 μm to about 150 μm.

8. The electrochemical device of claim 1, wherein the anode is printed directly onto the first metalized PLA film of the water vapor barrier.

9. The electrochemical device of claim 1, wherein the cathode is printed directly onto the second metalized PLA film of the water vapor barrier.

10. A water vapor barrier, comprising:
- a first metalized PLA film having a non-metalized side;
- a second metalized PLA film having a non-metalized side, wherein the non-metalized side of the first metalized PLA film faces the non-metalized side of the second metalized PLA film; and
  - wherein edge portions of the first and second metalized PLA films sealed together to define an interior configured to receive an electrochemical device.

11. The water vapor barrier of claim 10, wherein the first metalized PLA film or the second metalized PLA film comprises polylactic acid (PLA).

12. The water vapor barrier of claim 10, wherein the first metalized PLA film or the second metalized PLA film comprises a metal layer comprising aluminum.

13. The water vapor barrier of claim 10, further comprising multiple layers.

14. The water vapor barrier of claim 12, wherein the metal layer has a thickness of from about 1 μm to about 150 μm.

15. The water vapor barrier of claim 10, further comprising:
- an anode;
- a cathode; and
- an electrolyte composition disposed between the anode and the cathode; and
- wherein the anode, the cathode, and the electrolyte composition are enclosed by the water vapor barrier.

16. An electrochemical device comprising:
- an anode;
- a cathode;
- an electrolyte composition disposed between the anode and the cathode; and
- a water vapor barrier comprising a biodegradable material, wherein:
  - the water vapor barrier comprising the biodegradable material further comprises a first metalized PLA film and a second metalized PLA film, each having a non-metalized side, wherein the non-metalized side of the first metalized PLA film faces the non-metalized side of the second metalized PLA film, and peripheral edge portions of the first and second metalized PLA films are sealed together to enclose the electrochemical device; and
  - the electrochemical device has a water vapor transmission rate (WVTR) less than or equal to 1 mg per $cm^2$ over 24 hours.

17. The electrochemical device of claim 16, wherein the water vapor barrier further comprises multiple layers.

18. The electrochemical device of claim 16, wherein the first metalized PLA film or the second metalized PLA film comprises a metal layer having a thickness of from about 0.1 μm to about 10 μm.

19. The electrochemical device of claim 16, wherein the first metalized PLA film or the second metalized PLA film comprises a metal layer having a thickness of from about 20 μm to about 150 μm.

* * * * *